US012802792B2

(12) United States Patent
Takeyasu et al.

(10) Patent No.: US 12,802,792 B2
(45) Date of Patent: Nov. 17, 2026

(54) INFORMATION PROCESSING APPARATUS, DATA EXTRACTION METHOD, AND STORAGE MEDIUM

(71) Applicant: NEC Corporation, Tokyo (JP)

(72) Inventors: Koki Takeyasu, Tokyo (JP); Yasushi Takahashi, Tokyo (JP); Masashi Murao, Tokyo (JP); Takeshi Tatebe, Tokyo (JP); Michio Kaji, Tokyo (JP); Masayuki Naitou, Tokyo (JP)

(73) Assignee: NEC CORPORATION, Tokyo (JP)

( * ) Notice: Subject to any disclaimer, the term of this patent is extended or adjusted under 35 U.S.C. 154(b) by 0 days.

(21) Appl. No.: 18/975,160

(22) Filed: Dec. 10, 2024

(65) Prior Publication Data

US 2025/0210159 A1 Jun. 26, 2025

(30) Foreign Application Priority Data

Dec. 20, 2023 (JP) ................................ 2023-215084

(51) Int. Cl.
*G16H 10/60* (2018.01)

(52) U.S. Cl.
CPC .................................. *G16H 10/60* (2018.01)

(58) Field of Classification Search
CPC ......... G06F 16/35; G16Z 99/00; G16H 10/60; G16H 15/00
USPC ........................................................ 705/2, 3
See application file for complete search history.

(56) References Cited

U.S. PATENT DOCUMENTS 11,152,084 B2 * 10/2021 Kondadadi ............. G16Z 99/00
11,250,856 B2 * 2/2022 Montyne ................ G16H 15/00
2016/0239564 A1 * 8/2016 Sohma .................... G06F 16/35
2021/0118568 A1 * 4/2021 Mitsumori ............. G16H 10/60

FOREIGN PATENT DOCUMENTS

| | | | | | |
|---|---|---|---|---|---|
| AU | 2017362240 | A1 | * | 6/2019 | G16H 15/00 |
| CN | 109616215 | B | * | 7/2021 | G16H 50/70 |
| CN | 117542487 | A | * | 2/2024 | G16H 30/20 |
| CN | 114049929 | B | * | 12/2024 | G16H 10/60 |
| FR | 2953961 | A1 | * | 6/2011 | G16H 10/60 |
| JP | 2002-203044 | A | | 7/2002 | |
| JP | 2008-021041 | A | | 1/2008 | |
| JP | 2008-532104 | A | | 8/2008 | |
| JP | 2017-502439 | A | | 1/2017 | |
| JP | 2021-056641 | A | | 4/2021 | |
| KR | 20200139863 | A | * | 12/2020 | G16H 10/60 |

* cited by examiner

*Primary Examiner* — Dilek B Cobanoglu
(74) *Attorney, Agent, or Firm* — Sughrue Mion, PLLC

(57) ABSTRACT

To cause observation data to be easily available. An information processing apparatus includes a reception section that receives designation of an extraction condition on observation data and an extraction section that, in a case where the designation is received, starts a process of extracting a piece of observation data which, among observation data that has been stored after reception of the designation, matches the extraction condition and storing the piece of observation data in a database. The observation data stored in the database can be used, for example, for decision making for a countermeasure against an infectious disease.

6 Claims, 7 Drawing Sheets

INFORMATION PROCESSING APPARATUS, DATA EXTRACTION METHOD, AND STORAGE MEDIUM

CROSS REFERENCE TO RELATED APPLICATIONS

This application is based upon and claims the benefit of priority from Japanese Patent Application No. 2023-215084 filed on Dec. 20, 2023, the disclosure of which is incorporated herein in its entirety by reference.

TECHNICAL FIELD

The present disclosure relates to an information processing apparatus, a data extraction method, and a storage medium.

BACKGROUND ART

Development of technologies to cause medical information to more easily available is under way. For example, Patent Literature 1 discloses a medical information management server that provides metadata for retrieval to an image interpretation report which is associated with an image generated with use of, for example, magnetic resonance imaging (MRI) and which has text data of observation by an image interpretation doctor.

CITATION LIST

Patent Literature

[Patent Literature 1]
Japanese Patent Application Publication Tokukai No. 2021-56641

SUMMARY OF INVENTION

Technical Problem

Providing metadata with use of the medical information management server disclosed in Patent Literature 1 improves convenience for using past observation data accumulated. However, this medical information management server is insufficient for easier availability of observation data continually generated and has room for improvement.

For example, in worldwide prevalence of a viral infectious disease that has recently occurred, there has been a need to monitor and analyze a state of its spread. However, in order to carry out such monitoring and analysis, it is required to endlessly continue operation of manually collecting and classifying observation data continually generated in, for example, medical institutions and health centers, which consumes enormous human and time costs. The medical information management server disclosed in Patent Literature 1 does not contribute to addressing such an issue.

An example object of the present disclosure is to provide a technology that causes observation data continually generated to be easily available.

Solution to Problem

An information processing apparatus in accordance with one example aspect of the present disclosure includes at least one processor, the at least one processor being configured to: receive designation of an extraction condition on observation data indicating an examination content of a patient; and in a case where the designation is received, start a process of extracting a piece of observation data which, among observation data that has been stored in at least one target medical institution after reception of the designation, matches the extraction condition designated and storing the piece of observation data in a database.

A data extraction method in accordance with one example aspect of the present disclosure includes: a reception process of, by at least one processor, receiving designation of an extraction condition on observation data indicating an examination content of a patient, the at least one processor, in a case where the reception process is carried out, starting a process of extracting a piece of observation data which, among observation data that has been stored in at least one target medical institution after reception of the designation, matches the extraction condition designated and storing the piece of observation data in a database.

A storage medium of one example aspect of the present disclosure is a computer-readable non-transitory storage medium storing a data extraction program that causes a computer to: carry out a reception process of receiving designation of an extraction condition on observation data indicating an examination content of a patient; and in a case where the designation is received, start a process of extracting a piece of observation data which, among observation data that has been stored in at least one target medical institution after reception of the designation, matches the extraction condition designated and storing the piece of observation data in a database.

Advantageous Effects of Invention

An example aspect of the present disclosure exerts an example advantage of successfully providing a technology that causes observation data continually generated to be easily available.

EXAMPLE EMBODIMENTS

Figure 1:
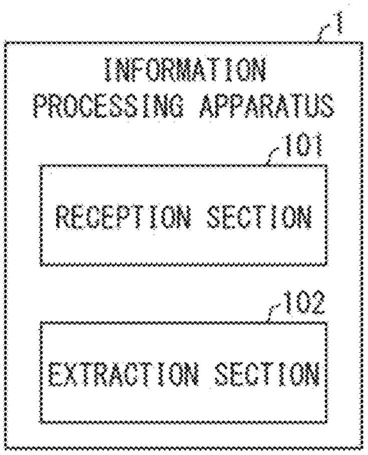
FIG. 1 is a block diagram illustrating a configuration of an information processing apparatus in accordance with the present disclosure.

The following description will discuss example embodiments of the present invention. The present invention is not limited to the example embodiments below, but may be altered in various ways by a skilled person within the scope of the claims. For example, any example embodiment derived by appropriately combining technical means disclosed in the example embodiments below can also be within the scope of the present invention. For example, any example embodiment derived by appropriately omitting one or more of the technical means adopted in the example embodiments below can also be within the scope of the present invention. An example advantage mentioned in each of the example embodiments below is an example of an advantage that is expected in that example embodiment, and is not intended to define an extension of the present invention. That is, any embodiment that does not provide the example advantage mentioned in each of the example embodiments below can also be within the scope of the present invention.

First Example Embodiment

The following description will discuss a first example embodiment, which is an example embodiment of the present invention, in detail with reference to the drawings. The present example embodiment is basic to example embodiments described later. It should be noted that the applicable scope of each technical means adopted in the present example embodiment is not limited to the present example embodiment. That is, each technical means adopted in the present example embodiment can be adopted in another example embodiment included in the present disclosure, to the extent of constituting no specific technical obstacle. Further, each technical means illustrated in the drawings which are referred to for describing the present example embodiment can be adopted in another example embodiment included in the present disclosure, to the extent of constituting no specific technical obstacle.

(Configuration of Information Processing Apparatus 1)

With reference to FIG. 1, the following will describe a configuration of the information processing apparatus 1. FIG. 1 is a block diagram illustrating a configuration of the information processing apparatus 1. As illustrated in the drawing, the information processing apparatus 1 includes a reception section 101 and an extraction section 102.

The reception section 101 receives designation of an extraction condition on observation data indicating contents of examination of a patient. There is no particular limitation on a method for receiving the designation. For example, in a case where the information processing apparatus 1 includes an input apparatus, the reception section 101 may receive designation via the input apparatus. For example, in a case where the information processing apparatus 1 has a communication function, the reception section 101 may use the communication function to receive designation from external equipment.

The observation data only needs to indicate the examination contents of a patient. The observation data may include, for example, data indicating contents of examination by a doctor and a result of the examination, data indicating a result of inspection, data indicating medication instruction, and vital data of a patient. In addition, the observation data may include, for example, data indicating a gender of a patient, a birth date of a patient, an examination date of a patient, and a medical institution in which a patient has been examined.

In a case where the reception section 101 receives designation of an extraction condition, the extraction section 102 starts a process of extracting a piece of observation data which, among observation data that has been stored in at least one target medical institution after reception of the designation, matches the extraction condition designated and storing the piece of observation data in a database. Therefore, the user of the information processing apparatus 1 merely designates an extraction condition for extracting desired observation data, so that desired observation data will be accumulated in the database, among observation data continually generated in a plurality of medical institutions.

Note that the database may be included in the information processing apparatus 1 or may be provided outside the information processing apparatus 1. The term "medical institution" refers to an institution that generates observation data indicating examination contents of a patient. For example, a health center that inspects whether a patient is infected with a specific infectious disease and generates observation data indicating a result of the inspection is also within the scope of the above "medical institution".

As described above, the information processing apparatus 1 includes the reception section 101 configured to receive designation of an extraction condition on observation data indicating an examination content of a patient; and the extraction section 102 configured to, in a case where the designation is received by the reception section 101, start a process of extracting a piece of observation data which, among observation data that has been stored in at least one target medical institution after reception of the designation, matches the extraction condition designated and storing the piece of observation data in a database. Therefore, the information processing apparatus 1 in accordance with the present example embodiment provides an example advantage of causing observation data continually generated to be easily available.

For example, in a case where spread of a specific infectious disease is suspected, a user designates a symptom typical of the infectious disease as an extraction condition, so that it is possible to cause observation data of a patient suffering from the infectious disease to be accumulated in a database. The user in this case may be, for example, a public institution. This makes it possible to narrow down target observation data for monitoring or analyzing the spread of the infectious disease to that accumulated in the database, so that the availability of the observation data is improved. Further, for example, the observation data stored in the database can be used for decision making for a countermeasure against an infectious disease.

(Data Extraction Program)

The functions of the information processing apparatus 1 above can also be implemented by a program. A data extraction program in accordance with the present example embodiment causes a computer to function as: reception means for receiving designation of an extraction condition on observation data indicating an examination content of a patient; and extraction means for, in a case where the designation is received, starting a process of extracting a piece of observation data which, among observation data that has been stored in at least one target medical institution after reception of the designation, matches the extraction condition designated and storing the piece of observation data in a database. Therefore, the data extraction program in accordance with the present example embodiment provides an example advantage of causing observation data continually generated to be easily available.

(Flow of Data Extraction Method)

Figure 2:
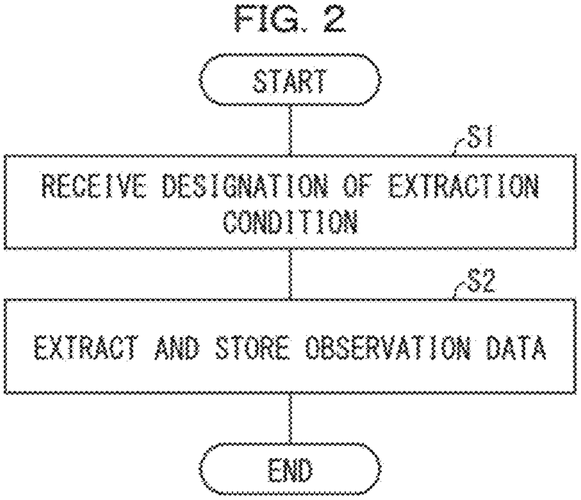
FIG. 2 is a flowchart illustrating a flow of a data extraction method in accordance with the present disclosure.

With reference to FIG. 2, the following will describe a flow of the data extraction method. FIG. 2 is a flowchart illustrating a flow of a data extraction method in accordance with the present disclosure. Each of the steps of the data extraction method may be carried out by a processor included in the information processing apparatus 1, or may be carried out by a processor included in another apparatus. Alternatively, the steps may be carried out by respective processors provided in different apparatuses.

In S1 (reception process), at least one processor receives designation of an extraction condition on observation data indicating contents of examination of a patient.

In S2 (extraction process), at least one processor extracts a piece of observation data which, among observation data stored in at least one target medical institution after reception of the designation in S1, matches the extraction condition designated, and stores the piece of observation data in a database.

Note that the process of S2 may be carried out by, for example, acquiring, at a time, pieces of observation data which have been stored after the reception of the designation in S1, and from among them, extracting a piece of observation data which matches the extraction condition. Alternatively, the process of S2 may be, for example, carried out by repeating a series of processes of, each time new observation data is stored after the reception of the designation in S1, acquiring observation data and storing the acquired observation data in a database if it matches the extraction condition.

As described above, a data extraction method in accordance with the present example embodiment of the present disclosure includes: a reception process of receiving designation of an extraction condition on observation data indicating an examination content of a patient; and an extraction process of extracting a piece of observation data which, among observation data that has been stored in at least one target medical institution after reception of the designation, matches the extraction condition designated and storing the piece of observation data in a database, the reception process and the extraction process being carried out by at least one processor, the extraction process being started in a case where the reception process is carried out. Therefore, an example advantage is provided of causing observation data continually generated to be easily available.

Second Example Embodiment

The following description will discuss a second example embodiment, which is an example embodiment of the present invention, in detail with reference to the drawings. It should be noted that the applicable scope of each technical means adopted in the present example embodiment is not limited to the present example embodiment. That is, each technical means adopted in the present example embodiment can be adopted in another example embodiment included in the present disclosure, to the extent of constituting no specific technical obstacle. Further, each technical means illustrated in the drawings which are referred to for describing the present example embodiment can be adopted in another example embodiment included in the present disclosure, to the extent of constituting no specific technical obstacle.

(Configuration of Data Extraction System 7A)

Figure 3:
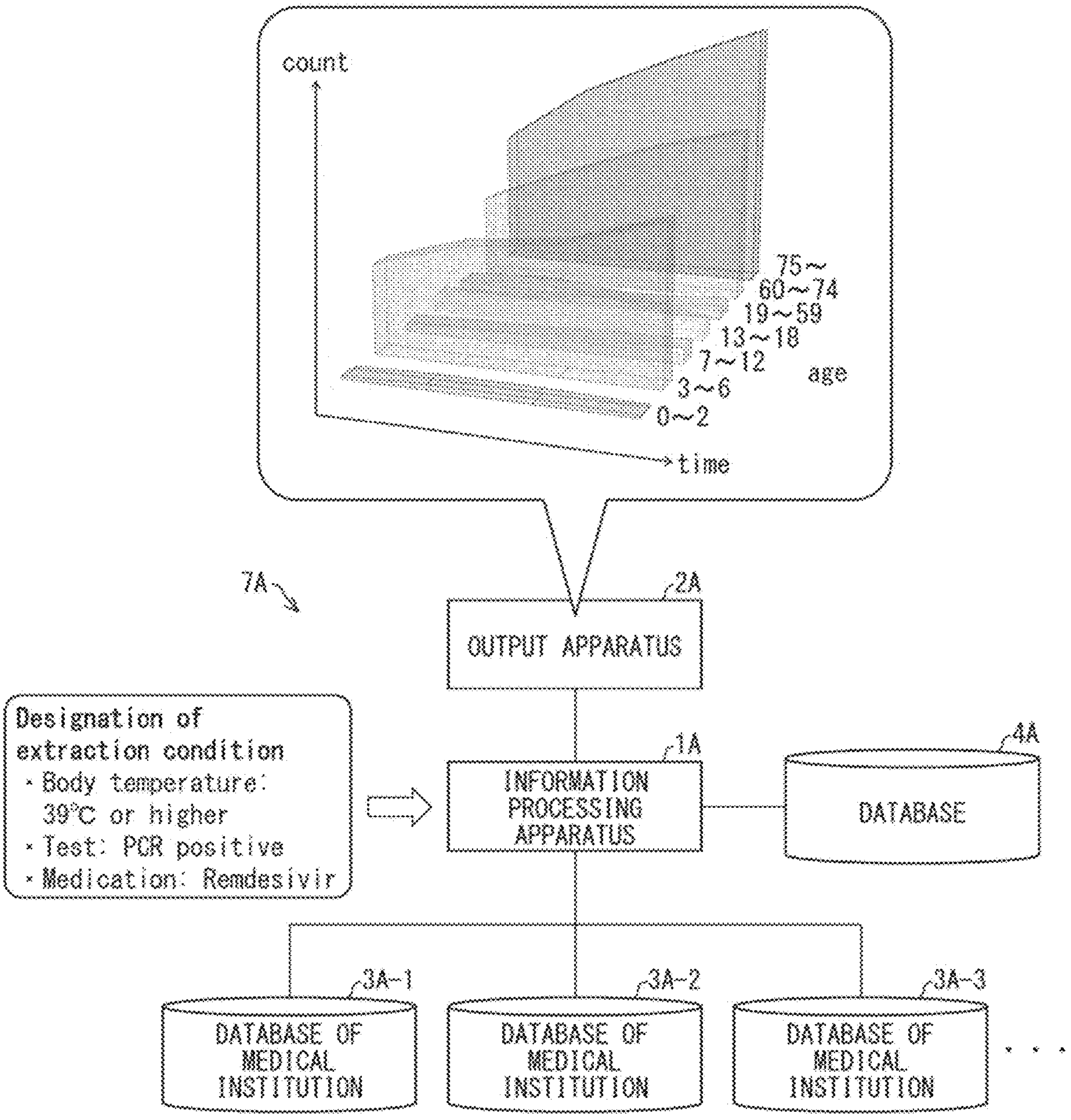
FIG. 3 is a view illustrating an overview of a data extraction system in accordance with the present disclosure.

With reference to FIG. 3, the following will discuss a configuration of a data extraction system 7A. FIG. 3 is a view illustrating an overview of the data extraction system 7A. As illustrated in the drawing, the data extraction system 7A includes an information processing apparatus 1A, an output apparatus 2A, databases 3A-1 to 3A-3 of medical institutions, and a database 4A that stores observation data which has been extracted. The databases 3A-1 to 3A-3 of the medical institutions are each, in a case where not required to be distinguished, referred to simply as "database 3A". The number of the databases 3A included in the data extraction system 7A, in other words, the number of target medical institutions from which observation data is to be extracted can be set as appropriate, and is not limited to the illustrated example.

The data extraction system 7A has a function, which will be described later in detail, of storing, in the database 4A, observation data that matches an extraction condition designated by a user, among pieces of observation data that are generated in the target medical institutions and stored in the databases 3A-1 to 3A-3 regularly. The function is achieved by the information processing apparatus 1A.

The output apparatus 2A has a function of outputting data. There is no particular limitation on how the output apparatus 2A outputs the data. For example, the output apparatus 2A may output data by displaying, or by printing, or by sound, or by any combination thereof. The following description will discuss an example in which the output apparatus 2A is an apparatus that outputs data by displaying, that is, an example in which the output apparatus 2A is a display apparatus. Note that in a case where the information processing apparatus 1A includes an output apparatus, it is possible to cause the output apparatus to output the data and omit the output apparatus 2A.

The databases 3A are each a database that stores observation data generated in the corresponding one of the target medical institutions. As described above, the number of the target medical institutions and the number of the databases 3A can be set as appropriate. For example, the target medical institutions from which the observation data is to be extracted by the data extraction system 7A may be medical institutions throughout the country. Note that it is possible that databases 3A are each provided in one medical institution, and it is also possible that pieces of observation data of a plurality of medical institutions are collectively stored in one database 3A. Further, data stored in the database 3A may be inputted to the information processing apparatus 1A via another apparatus.

The database 4A is a database that stores observation data that has been extracted by the information processing apparatus 1A. FIG. 3 shows an example in which the data extraction system 7A illustrated is provided with the database 4A that is disposed outside the information processing apparatus 1A. However, the database 4A may be disposed inside the information processing apparatus 1A.

Here, for example, as illustrated in FIG. 3, assume that an extraction condition that a body temperature is not less than 39° C., a result of a polymerase chain reaction (PCR) test for COVID-19 is positive, and remdesivir is to be administered is designated. In this case, the information processing apparatus 1A that has been received designation of the extraction condition starts, in a case where the designation is received, a process of extracting a piece of observation data which, among observation data that has been stored in the databases 3A after reception of the designation, matches the extraction condition designated and storing the piece of observation data in the database 4A.

By doing so, observation data of patients who have a body temperature of not less than 39° C. and have received a positive result of a PCR test for COVID-19 and to whom remdesivir is to be administered will be accumulated in the database 4A. Then, this also facilitates analysis on patients as described above. For example, the information processing apparatus 1A also can generate a graph as illustrated with use of observation data accumulated in the database 4A and cause the output apparatus 2A to display this.

The graph illustrated in FIG. 3 shows transitions, by age group, of the number of patients who have a body temperature of not less than 39° C. and have received a positive result of a PCR test for COVID-19 and to whom remdesivir is to be administered (specifically, the number of times in which such diagnosis has been made), with the three axes of time, age, and count. Displaying such a graph enables an easy understanding of a transition of a tendency of medication instruction for patients in each age group. The data extraction system 7A also can extract and accumulate observation data related to another infectious disease or illness, such as influenza, instead of COVID-19. That is, the data extraction system 7A can be used for monitoring, analysis, and the like of any infectious disease or illness.

(Configuration of Information Processing Apparatus 1A)

Figure 4:
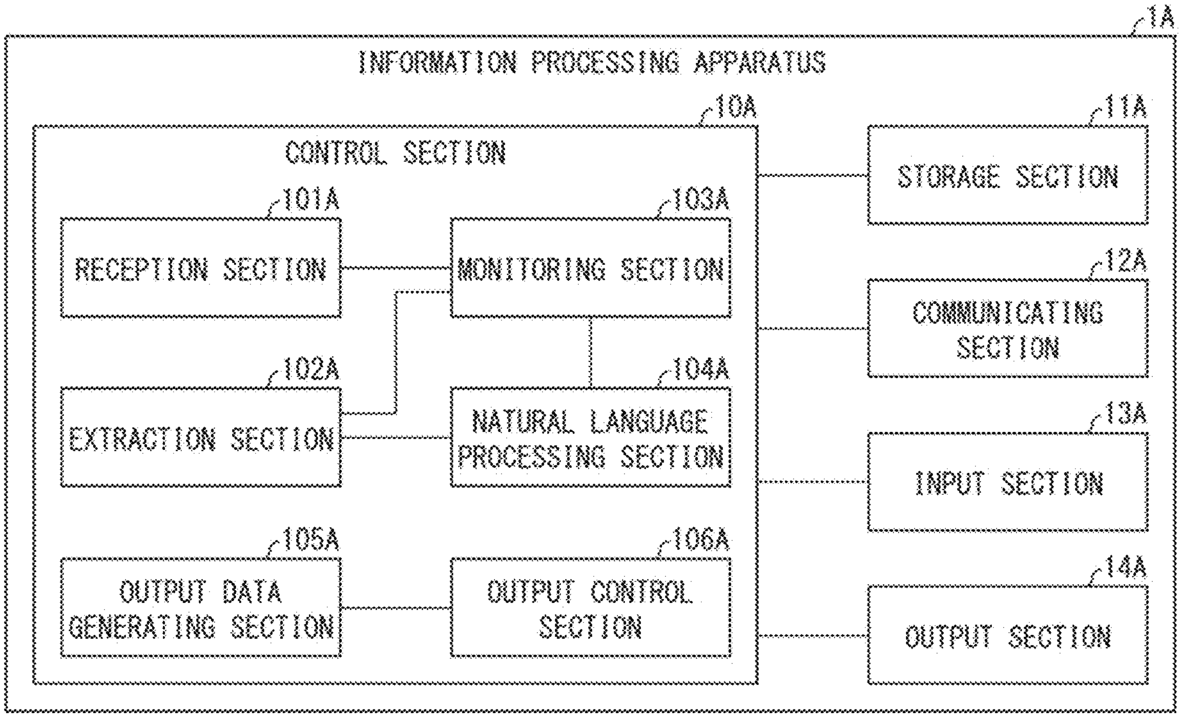
FIG. 4 is block diagram illustrating a configuration of another information processing apparatus in accordance with the present disclosure.

With reference to FIG. 4, the following will describe a configuration of the information processing apparatus 1A. FIG. 4 is a block diagram illustrating a configuration example of the information processing apparatus 1A. As illustrated in the drawing, the information processing apparatus 1A includes: a control section 10A that performs overall control of the sections of the information processing apparatus 1A; and a storage section 11A that stores various kinds of data used by the information processing apparatus 1A. In addition, the information processing apparatus 1A includes: a communicating section 12A via which the information processing apparatus 1A communicates with another apparatus; an input section 13A that accepts an input to the information processing apparatus 1A; and an output section 14A via which the information processing apparatus 1A outputs various kinds of data. Further, the control section 10A includes a reception section 101A, an extraction section 102A, a monitoring section 103A, a natural language processing section 104A, an output data generating section 105A, and an output control section 106A.

As with the reception section 101 in accordance with the first example embodiment, the reception section 101A receives designation of an extraction condition on observation data indicating contents of examination of a patient. For example, the extraction condition may be at least any one of a chief complaint of a patient, a time point at which the symptom has begun to appear, a behavior of a symptom, a strength of a symptom, presence or absence of remission, presence or absence of exacerbation, a part at which a symptom occurs, an accompanying symptom, chronological progression of a symptom, a treatment plan such as medication instruction, and a result of inspection.

As with the extraction section 102 in accordance with the first example embodiment, in a case where the reception section 101A receives the designation, the extraction section 102A starts a process of extracting a piece of observation data which, among observation data that has been stored in at least one target medical institution after reception of the designation, matches the extraction condition designated and storing the piece of observation data in the database 4A. In order to cause the stored observation data to be easily available, it is preferable that the extraction section 102A store the observation data after structuring the observation d predetermined format.

A user of the data extraction system 7A may designate, as appropriate, an extraction condition according to a usage of the observation data. For example, in a case where a specific symptom or syndrome is monitored or analyzed, an extraction condition indicating the symptom may be designated. By doing so, the extraction section 102A stores observation data indicating that a patient has the symptom, in the database 4A. Therefore, the information processing apparatus 1A provides an example advantage of facilitating monitoring and analysis of a specific symptom, in addition to the example advantage provided by the information processing apparatus 1.

The monitoring section 103A monitors storing of observation data in the databases 3A. In a case where the monitoring section 103A detects that new observation data has been stored in the database 3A, the monitoring section 103A acquires the stored observation data from the database 3A. The monitoring section 103A starts monitoring in a case where the reception section 101A receives designation of an extraction condition.

Note that the monitoring section 103A may access the database 3A after a predetermined time period since the reception section 101A had received designation of an extraction condition, and acquire, at a time, pieces of observation data which have been stored during the predetermined time period. The monitoring section 103A may repeat this process at predetermined time intervals. It is alternatively possible that after a predetermined operation has been carried out by the user, the monitoring section 103A acquires, at a time, pieces of observation data which have been stored during a time period from a time point at which the reception section 101A had received designation of an extraction condition to a time point at which the predetermined operation has been carried out.

The natural language processing section 104A is configured to enable determination of whether or not observation data including an examination content described in a natural language matches the extraction condition. The detail of the natural language processing section 104A will be described later in the section "Example 2 of method for extracting observation data".

The output data generating section 105A generates output data with use of the observation data stored in the database 4A. The output data only needs to be one according to a usage of the observation data. For example, in a case where a specific symptom or syndrome is to be monitored, the symptom may be designated as an extraction condition. In this case, the output data SC generating section 105A may generate output data indicating a feature of the symptom.

For example, the output data generating section 105A may generate, as output data, data (e.g., a graph) showing a transition of the number of patients diagnosed with the syndrome to be monitored (or the number of times in which diagnosis with the syndrome has been made). In addition to this, for example, the output data generating section 105A may generate statistical data on the observation data stored in the database 4A (e.g., an average age of patients diagnosed with the specific syndrome). The transition of the number of patients and the statistical data may be categorized by, for example, age groups, genders, and areas. Alternatively, for example, the output data generating section 105A may subject the observation data stored in the database 4A to causal analysis and generate output data (e.g., causal graph) indicating a result of the analysis. This can contribute to investigation of a cause of the syndrome and study of effective countermeasures.

The output control section 106A causes the output apparatus 2A to output data. For example, in a case where the output apparatus 2A is a display apparatus, the output control section 106A causes the output apparatus 2A to display characters or images. There is no particular limitation on contents of the data outputted by the output apparatus 2A. For example, the output control section 106A may cause the output apparatus 2A to display an image or a character string prompting input of an extraction condition or to display the output data generated by the output data generating section 105A. As described above, the output data may be, for example, data indicating a feature of a symptom indicated by the designated extraction condition. The output control section 106A may cause the output section 14A to output data.

As described above, the information processing apparatus 1A includes the output control section 106A that causes the output apparatus 2A to output data that has been generated with use of the observation data stored in the database 4A and that indicates a feature of a symptom indicated by an extraction condition. Here, in a case where the extraction section 102A stores new observation data in the database 4A, the output data generating section 105A may update the output data with use of the new observation data stored. Further, in a case where the extraction section 102A has stored the new observation data in the database 4A, the output control section 106A may update the output data to be outputted by the output apparatus 2A, so that the output data reflects the new observation data. This provides an example advantage of making it possible to monitor observation data on a real-time basis, in addition to the example advantage exerted by the information processing apparatus 1.

(Example 1 of Method for extracting Observation Data)

Figure 5:
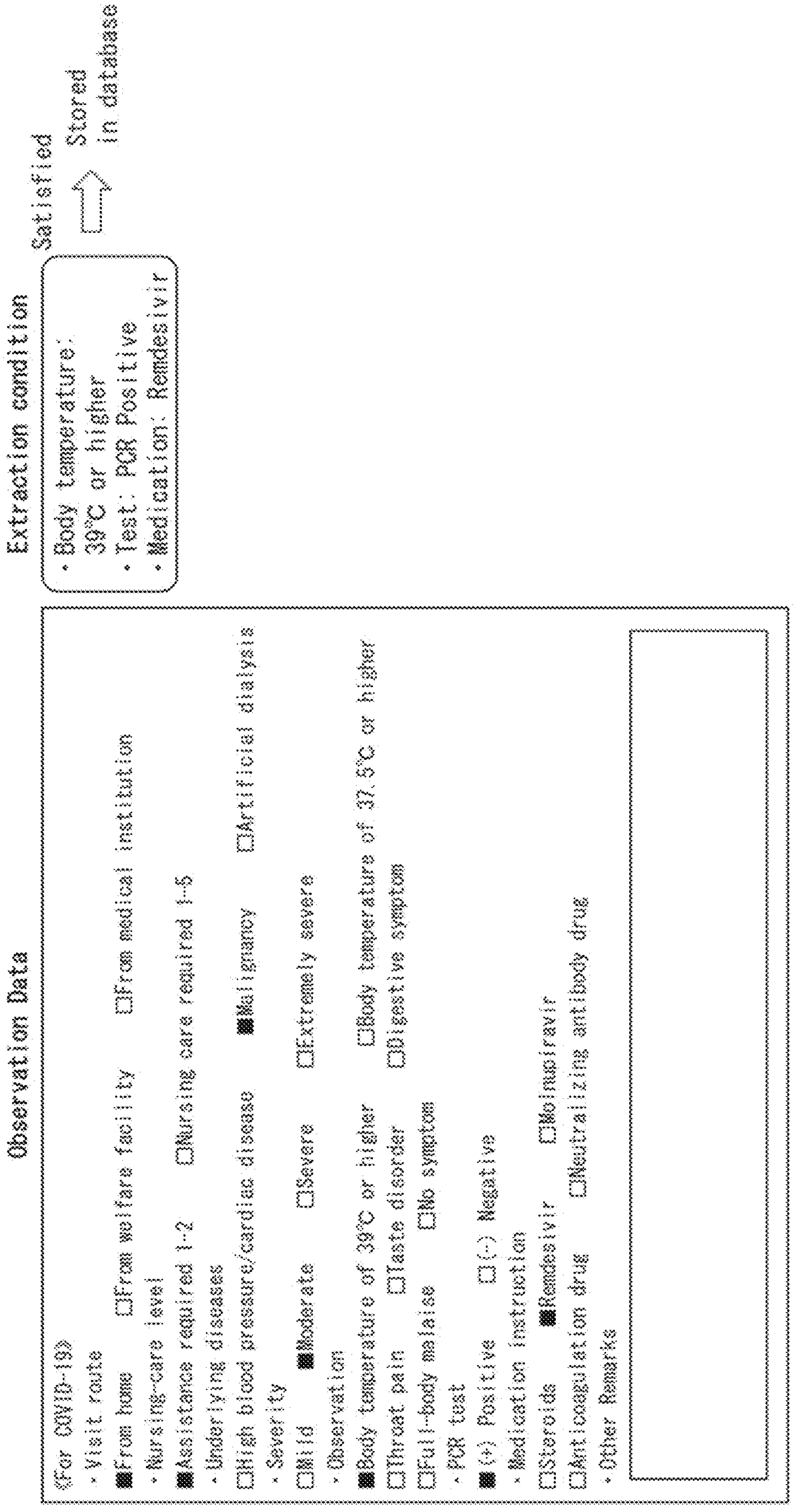
FIG. 5 is a view for explaining a method for determining whether or not an extraction condition is satisfied in a case where observation data is an electronic medical record.

With reference to FIG. 5, the following will describe a method for extracting observation data. FIG. 5 is a view for explaining a method for determining whether or not an extraction condition is satisfied in a case where observation data is an electronic medical record. Note that the extraction condition in the example shown in FIG. 5 is the same as that in the example shown in FIG. 3.

The observation data illustrated in FIG. 5 includes examination items for COVID-19. Specifically, the observation data includes a plurality of data items regarding examination, such as a visit route, to which the examination contents have been input. The observation data is generated by inputting the examination contents to an electronic medical record including a plurality of data items. That is, the observation data as illustrated in the drawing can be easily generated by having, for example, a doctor use an electronic medical record including a plurality of data items and structured so as to enable examination contents to be inputted to the data items. Note that it is possible that the electronic medical record into which the examination contents have been inputted is used as-is as observation data, and it is also possible that the values of the data items which have been extracted from the electronic medical record and associated with the corresponding data items are used as observation data.

Note that although the observation data illustrated in FIG. 5 has the data items in a format such that one of a plurality of options which corresponds to an examination content is selected, the data items of the observation data may include one to which a numerical value (e.g., a body temperature) has been inputted. Further, the observation data may include data indicating, for example, personal information such as a name, a birth date, a gender, and an address of a patient, an examination institution, an area where examination was carried out, a location of infection, an examination date, and a doctor in charge.

As described above, the observation data may be generated by inputting the examination contents to the plurality of data items of the electronic medical record. In this case, the extraction section 102A determines, based on the values of the data items corresponding to the extraction condition in the electronic medical record, whether or not the observation data matches the extraction condition. This provides an example advantage of making it possible to accurately extracting observation data matching an extraction condition, in addition to the example advantage exerted by the information processing apparatus 1.

Here, for example, as illustrated in FIG. 5, assume that an extraction condition that a body temperature is not less than 39° C., a result of a PCR test is positive, and remdesivir is to be administered is designated. In this case, the extraction section 102A refers to values of data items corresponding to this extraction condition in the electronic medical record, that is, refers to the values of the data items "observation", "PCR test", and "medication instruction". From these values, the extraction section 102A then determines whether or not the observation data matches the extraction condition. In the observation data illustrated in FIG. 5, the option "body temperature of not less than 39° C." is selected in the "observation", the option "(+) positive" is selected in the "PCR test", and the option "remdesivir" is selected in the "medication instruction". Therefore, this observation data is determined to match the extraction condition, and the observation data is stored in the database 4A.

Note that the extraction section 102A does not need to store, in the database 4A, all the pieces of data included in observation data (in other words, a completed electronic medical record), and the pieces of data to be stored may be narrowed down to data to be used. For example, the extraction section 102A may store, in the database 4A, observation data that has been anonymized by removing personal information, such as a patient name, from the observation data. This enables utilization of observation data considering protection of personal information. In a case where a syndrome is designated as an extraction condition, the extraction section 102A may extract data related to the syndrome from the observation data and store the data in the database 4A. Data items to be stored in the database 4A may be designated by a user.

The data items in the electronic medical record can be set as appropriate. Therefore, there may be cases where the data items set in each of the types of electronic medical records differ among the types. In some cases, for example, a body temperature is, as in the example illustrated in FIG. 5, stored in the data item "observation" in an electronic medical record provided by one vendor, while a body temperature is stored in another data item such as "body temperature" in an electronic medical record provided by another vendor.

In order to address the above issue, the extraction section 102A may apply a conversion rule according to the type of the electronic medical record, the conversion rule converting each of the plurality of data items included in the electronic medical record into a standard data item, and determine whether or not the observation data matches the extraction condition, in view of the plurality of data items after conversion. This provides an example advantage of making it possible to accurately extracting observation data matching an extraction condition, from among the plurality of types of electronic medical records, in addition to the example advantage exerted by the information processing apparatus 1.

(Example 2 of Method for Extracting Observation Data)

Figure 6:
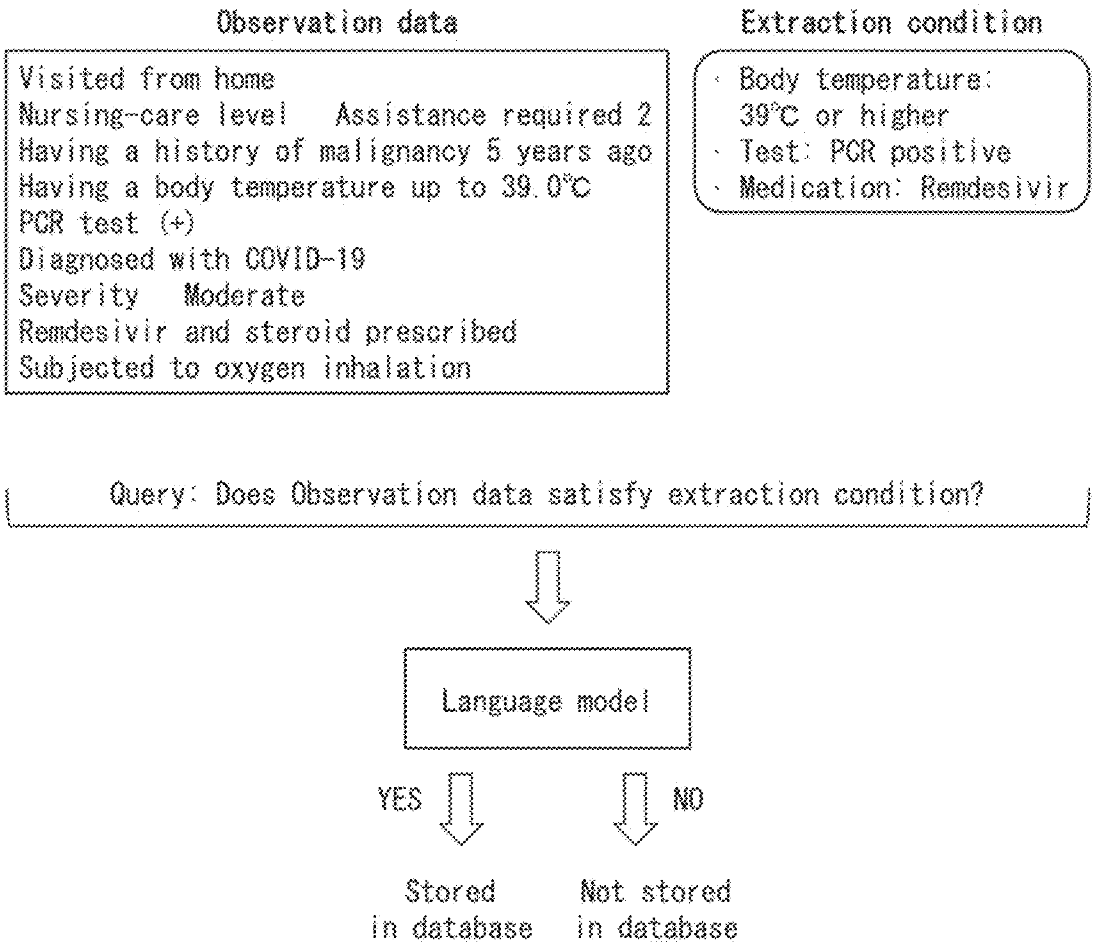
FIG. 6 is a view for explaining a method for determining whether or not observation data described in a natural language satisfies an extraction condition.

In the observation data, some or all of the examination contents may be described in a natural language. In this case, determination of whether or not the observation data satisfies the extraction condition can be made by using the function of the natural language processing section 104A. With reference to FIG. 6, the following will describe this.

FIG. 6 is a view for explaining a method for determining whether or not observation data described in a natural language satisfies an extraction condition.

In the observation data illustrated in FIG. 6, the examination contents are described in a natural language, but have similar contents to those of the observation data illustrated in FIG. 5. Further, the extraction condition in the example shown in FIG. 6 is the same as that in the example shown in FIG. 5. In a case where such observation data is acquired by the monitoring section 103A, the natural language processing section 104A inputs the examination contents described in a natural language which are included in the observation data, to a language model which has been trained by machine learning, and causes the language model to output data indicating whether or not the observation data matches the extraction condition.

Here, the "language model" used by the natural language processing section 104A is a model which has been trained by machine learning to be constructed through the machine learning so as to learn an arrangement of the components (e.g., words) in a sentence represented in a natural language and a sequence of sentences in a text. For example, the language model may be a model which has been trained by machine learning so as to generate an answer sentence in response to a question sentence represented in a natural language. The language model may be generated by machine learning using training data in which a set of observation data described in a natural language and an extraction condition is associated with, as correct answer data, whether or not the observation data matches the extraction condition. Alternatively, the language model may be a general-purpose language model that has been subjected to fine-tuning with the training data as described above.

For example, the natural language processing section 104A may input, to the language model, a query inquiring whether or not the examination contents satisfy the extraction condition, in addition to the examination contents shown in the observation data and the extraction condition, as illustrated in FIG. 6. Then, in a case where the answer outputted by the language model indicates that the extraction condition is satisfied, the extraction section 102A stores the observation data including the examination contents, in the database 4A (that is, the observation data is extracted). In contrast, in a case where the output from the language model indicates that the extraction condition is not satisfied, the extraction section 102A does not store the observation data including the examination contents, in the database 4A (that is, the observation data is not extracted).

In a case where part of the electronic medical record includes an examination content described in a natural language, the natural language processing section 104A may input the part to the language model and cause the language model to answer whether or not the part at least partially satisfies the extraction condition. In this case, the extraction section 102A may determine whether or not the extraction condition is satisfied, in view of the other part (structured part) of the electronic medical record and the above-described answer together. Alternatively, the natural language processing section 104A may input the entire electronic medical record that in part includes an examination content described in a natural language, to the language model and cause the language model to answer whether or not the electronic record satisfies the extraction condition.

As described above, the information processing apparatus 1A includes the natural language processing section 104A that inputs, to a language model which has been trained by machine learning, an examination content that is included in observation data and that is described in a natural language, and causes the language model to output data indicating whether or not the examination matches the extraction condition. The extraction section 102A then determines whether or not the observation data matches the extraction condition, in view of data outputted by the language model. This provides an example advantage of making it possible to accurately extract observation data that matches the extraction condition, even in a case where an examination content described in a natural language is included in the observation data, in addition to the example advantage exerted by the information processing apparatus 1.

The natural language processing section 104A may structure an examination content described in a natural language, with use of a language model. In this case, the extraction section 102A can use the structured examination content to determine whether or not observation data including the examination content matches an extraction condition. For example, the natural language processing section 104A may input, together with the observation data (that is described in a natural language) and the extraction condition, a query instructing that a description corresponding to the extraction condition be extracted from the observation data, to the language model. Thus, the description corresponding to the extraction condition is outputted from the language model, so that the natural language processing section 104A can structure the examination content with the extraction condition and the outputted description associated with each other.

For example, in the example illustrated in FIG. 6, the natural language processing section 104A may generate a query stating, "extract a measurement result of the body temperature from the observation data" using the keyword "body temperature" included in the extraction condition, and input the query to the language model. In this case, the data outputted from the language model indicates "39.0° C.". Therefore, the natural language processing section 104A can structure the examination content with a value of "39.0° C." associated with the data item "body temperature". The observation data thus structured can be used for determining whether or not the extraction condition is satisfied, as in the example illustrated in FIG. 5.

(Flow of Entire Process)

Figure 7:
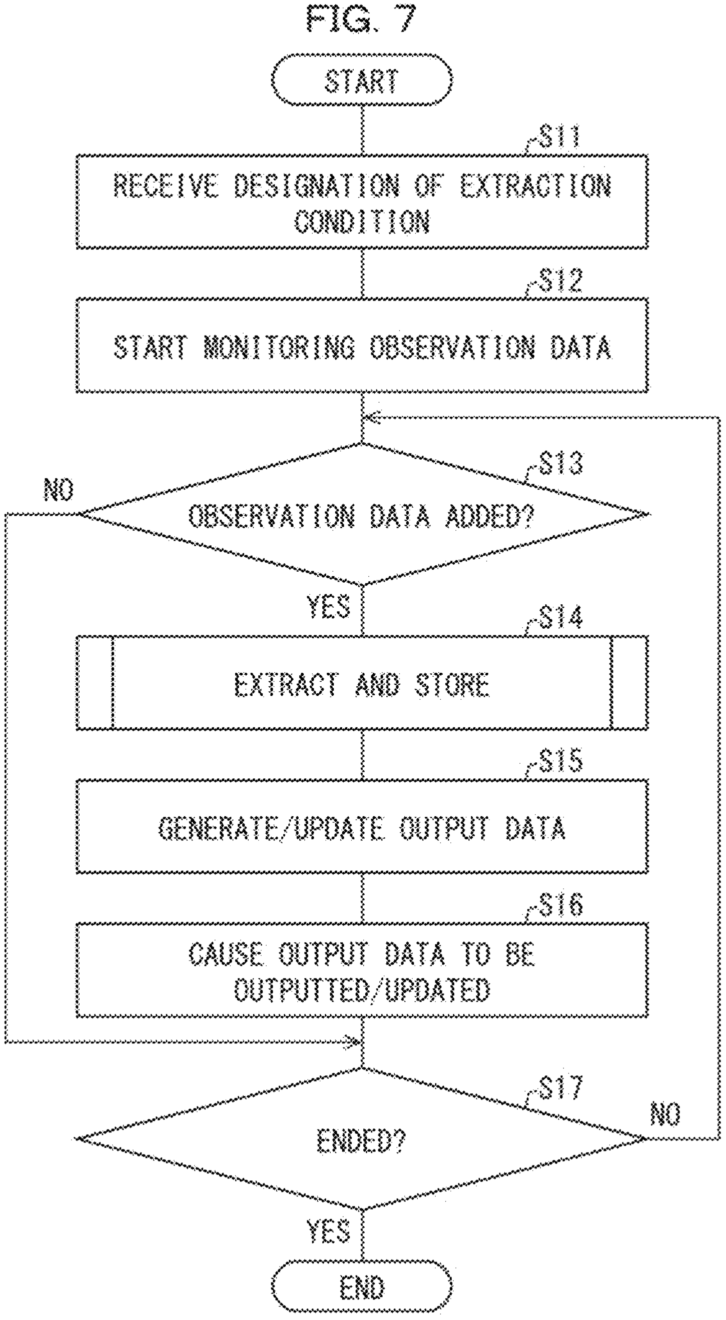
FIG. 7 is a flowchart illustrating a flow of example processes carried out by the information processing apparatus illustrated in FIG. 4.

With reference to FIG. 7, the following will describe a flow of a process carried out by the information processing apparatus 1A. FIG. 7 is a flowchart illustrating an example of a process carried out by the information processing apparatus 1A. FIG. 7 includes a data extraction method in accordance with the present example embodiment.

In S11 (reception process), the reception section 101A receives designation of an extraction condition. Subsequently, in S12, the monitoring section 103A starts monitoring observation data in the databases 3A. In S13, the monitoring section n 103A determines whether or not observation data is added to the databases 3A. In a case where the determination is YES in S13, the process proceeds to S14, and in a case where the determination is NO in S13, the process proceeds to S17.

In S14 (extraction process), the extraction section 102A carries out a process of extracting a piece of observation data which, among the observation data that has been stored after the reception of the designation in S11, matches the extraction condition designated and storing the piece of observation data in the database 4A. S14 is a process carried out in a case where the process of the S11 is carried out. The detail of S14 will be described later with reference to FIG. 8.

In S15, the output data generating section 105A generates output data with use of the observation data stored in S14. In S16, the output control section 106A then causes the output apparatus 2A to output the output data generated in S15. In the process of S15 in the second or subsequent cycle, the output data generating section 105A updates the output data with use of the observation data newly stored. In the subsequent S16, the output control section 106A updates the output data to be outputted by the output apparatus 2A.

Note that the configuration in which the processes of S15 and S16 are carried out after the process of S14 is effective, for example, in a case where a specific syndrome is constantly monitored. In a case where there is no need for the constant monitoring, the processes of S15 and S16 may be carried out in response to instruction by the user. Further, it is also possible that pieces of observation data which have been stored after the reception of the designation in S11 are acquired at a predetermined timing, and one that satisfies the extraction condition is extracted from among the pieces of observation data, instead of monitoring the addition of the observation data.

In S17, the monitoring section 103A determines whether to end the monitoring. In a case where the determination is YES in S17, the illustrated process is ended. In contrast, in a case where the determination is NO in S17, the process returns to S13. The condition for ending the monitoring may be determined as appropriate. For example, designation of a monitoring period may be received together with an extraction condition. In this case, elapse of the designated period is a condition for ending the monitoring.

(Flow of Process Related to Extraction and Storage of Observation Data)

Figure 8:
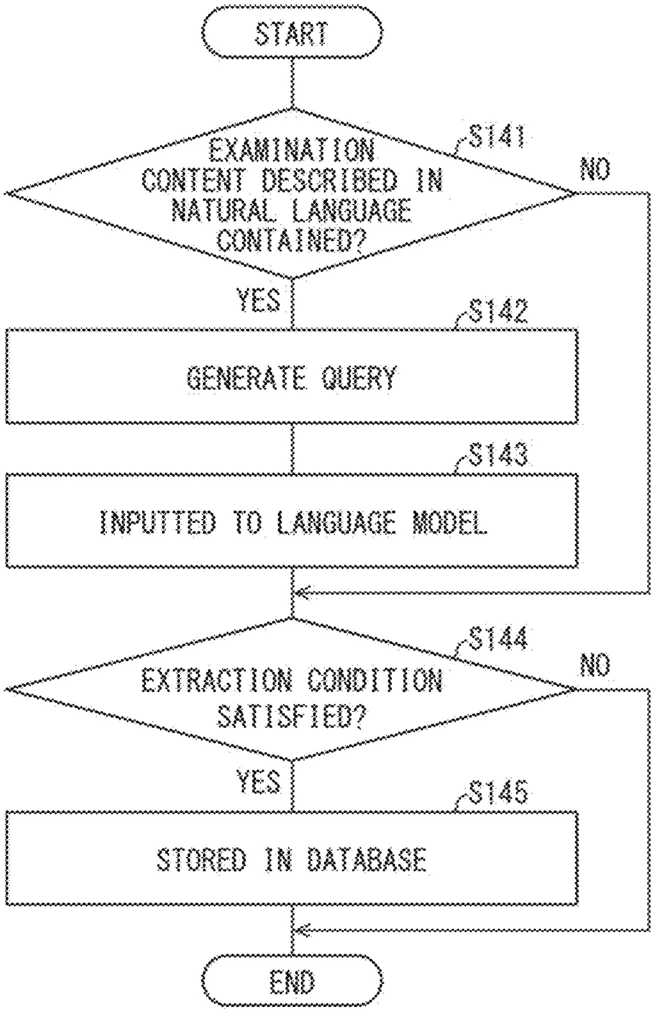
FIG. 8 is a flowchart illustrating a flow of a process related to extraction and storage of observation data.

With reference to FIG. 8, the following will describe the detail of the process of S14 in FIG. 7, that is, the detail of the process related to extraction and storage of observation data. FIG. 8 is a flowchart illustrating a flow of a process related to extraction and storage of observation data.

In S141, the natural language processing section 104A determines whether or not the observation data added includes an examination content described in a natural language. In a case where the determination is NO in S141, the process proceeds to S144, and in a case where the determination is YES in S141, the process proceeds to S142.

In S142, the natural language processing section 104A generates a query inquiring whether or not the examination content described in a natural language which is included in the observation data added satisfies the extraction condition. Subsequently, in S143, the natural language processing section 104A inputs the query generated in S142 to the language model and obtains an output from the language model.

In S144, the extraction section 102A determines whether or not the observation data added satisfies the extraction condition (that has been designated in S11 in FIG. 7). For example, in a case where the determination is NO in S141 and the process transitions to S144, the extraction section 102A may determine, based on a value of a data item corresponding to the extraction condition in the observation data, whether or not the observation data matches the extraction condition. In contrast, for example, in a case where the determination is YES in S141 and the process transitions to S144, the extraction section 102A may determine whether or not the observation data matches the extraction condition, on the basis of the output from the language model obtained in S143. Further, in a case where the observation data is an electronic medical record, the extraction section 102A may carry out the determination in S144 after applying a conversion rule according to the type of the electronic medical record.

In a case where the extraction section 102A determines NO in S144, the process is ended without storing the new observation data added, in the database 4A. In contrast, in a case where the extraction section 102A determines YES in S144, the process proceeds to S145, and the extraction section 102A stores the new observation data added, in the database 4A. Thus, the process of FIG. 8 ends.

[Variation]

A performer which carries out each of the processes described in the example embodiments above can be selected as appropriate, and is not limited to the above examples. That is, a data extraction system having a similar function to that of the information processing apparatus 1 or 1A can be constructed by a plurality of apparatuses capable of communicating with each other. For example, the processes in the flowchart illustrated in FIG. 2, FIG. 7, and FIG. 8 can be assigned to and be carried out by a plurality of apparatuses (in other words, processors).

[Software Implementation Example]

Some or all of the functions of each of the information processing apparatuses 1 and 1A may be implemented by hardware such as an integrated circuit (IC chip), or may be implemented by software.

Figure 9:
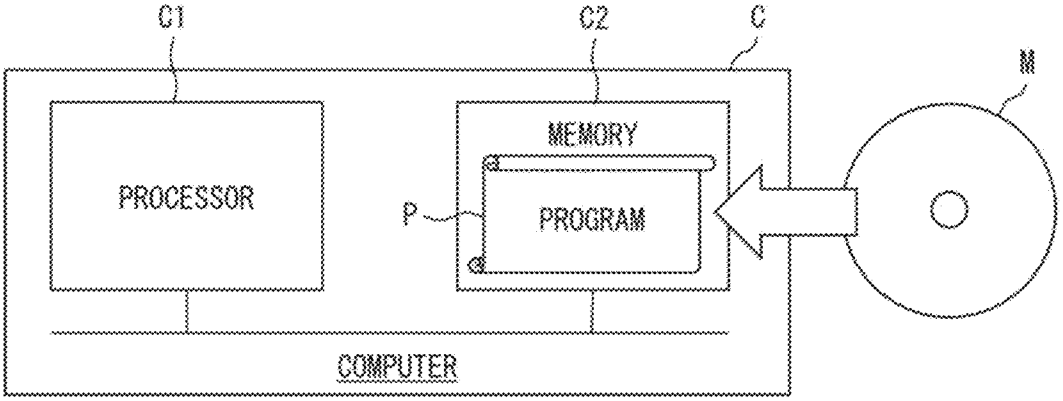
FIG. 9 is a block diagram illustrating a configuration of a computer which functions as the information processing apparatus in accordance with the present disclosure.

In the latter case, each of the information processing apparatuses 1 and 1 A is implemented by, for example, a computer that executes instructions of a program that is software implementing the foregoing functions. An example (hereinafter, computer C) of such a computer is illustrated in FIG. 9. FIG. 9 is a block diagram illustrating a configuration of the computer C which functions as the information processing apparatus 1 or 1A.

The computer C includes at least one processor C1 and at least one memory C2. The memory C2 has stored thereon a program (data extraction program) P for causing the computer C to operate as each apparatus above. The processor C1 of the computer C retrieves the program P from the memory C2 and executes the program P, so that the functions of the information processing apparatus 1 or 1A are implemented.

Examples of the at least one processor C1 can include a central processing unit (CPU), a graphic processing unit (GPU), a digital signal processor (DSP), a micro processing unit (MPU), a floating point number processing unit (FPU), a physics processing unit (PPU), a tensor processing unit (TPU), a quantum processor, a microcontroller, and a combination thereof. Examples of the memory C2 can include a flash memory, a hard disk drive (HDD), a solid state drive (SSD), and a combination thereof.

The computer C may further include a random access memory (RAM) into which the program P is loaded at the time of execution and in which various kinds of data are temporarily stored. The computer C may further include a communication interface via which data is transmitted to and received from another apparatus. The computer C may further include an input-output interface via which input-output equipment such as a keyboard, a mouse, a display or a printer is connected.

The program P can be stored on a non-transitory tangible storing medium M capable of being read by the computer C. Examples of such a storing medium M can include a tape, a disk, a card, a semiconductor memory, and a programmable logic circuit. The computer C can obtain the program P via such a storing medium M. The program P can be transmitted via a transmission medium. Examples of such a transmission medium can include a communication network and a broadcast wave. The computer C can also obtain the program P via such a transmission medium.

[Additional Remark]

The present disclosure includes techniques described in supplementary notes below. Note, however, that the present invention is not limited to the techniques described in supplementary notes below, but may be altered in various ways by a skilled person within the scope of the claims.

(Supplementary Note A1)

An information processing apparatus including reception means for receiving designation of an extraction condition on observation data indicating an examination content of a patient; and extraction means for, in a case where the designation is received, starting a process of extracting a piece of observation data which, among observation data that has been stored in at least one target medical institution after reception of the designation, matches the extraction condition designated and storing the piece of observation data in a database.

(Supplementary Note A2)

The information processing apparatus according to supplementary note A1, in which: the observation data is generated by inputting the examination content to a plurality of data items of an electronic medical record; and the extraction means determines, based on a value of at least one of the plurality of data items which corresponds to the extraction condition in the electronic medical record, whether or not the observation data matches the extraction condition.

(Supplementary Note A3)

The information processing apparatus according to supplementary note A2, in which the extraction means applies a conversion rule according to the type of the electronic medical record, the conversion rule converting each of the plurality of data items included in the electronic medical record into a standard data item, and determines whether or not the observation data matches the extraction condition, in view of the plurality of data items after conversion.

(Supplementary Note A4)

The information processing apparatus according to any one of supplementary notes A1 to A3, in which: the information processing apparatus includes natural language processing means for inputting, to a language model which has been trained by machine learning, an examination content that is included in the observation data and that is described in a natural language and causing the language model to output data indicating whether or not the examination content matches the extraction condition; and the extraction means determines whether or not the observation data matches the extraction condition, in view of the data outputted by the language model.

(Supplementary Note A5)

The information processing apparatus according to any one of supplementary notes A1 to A4, in which the extraction condition indicates at least one symptom, and the extraction means stores, in the database, the observation data indicating that the patient has the at least one symptom.

(Supplementary Note A6)

The information processing apparatus according to supplementary note A5, in which the information processing apparatus includes an output control section that causes an output apparatus to output data that has been generated with use of the observation data stored in the database and that indicates a feature of the at least one symptom, and in a case where new observation data is stored in the database by the extraction means, the output control section updates the output data to be outputted by the output apparatus, so that the output data reflects the new observation data.

(Supplementary Note B1)

A data extraction method including: a reception process of receiving designation of an extraction condition on observation data indicating an examination content of a patient; and an extraction process of extracting a piece of observation data which, among observation data that has been stored in at least one target medical institution after reception of the designation, matches the extraction condition designated and storing the piece of observation data in a database, the reception process and the extraction process being carried out by at least one processor, the extraction process being started in a case where the reception process is carried out.

(Supplementary Note B2)

The data extraction method according to supplementary note B1, in which: the observation data is generated by inputting the examination content to a plurality of data items of an electronic medical record; and in the extraction process, the at least one processor determines, based on a value of at least one of the plurality of data items which corresponds to the extraction condition in the electronic medical record, whether or not the observation data matches the extraction condition.

(Supplementary Note B3)

The data extraction method according to supplementary note B2, in which in the extraction process, the at least one processor applies a conversion rule according to the type of the electronic medical record, the conversion rule converting each of the plurality of data items included in the electronic medical record into a standard data item, and determines whether or not the observation data matches the extraction condition, in view of the plurality of data items after conversion.

(Supplementary Note B4)

The data extraction method according to any one of supplementary notes B1 to B3, in which: the data extraction method includes a process of, by the at least one processor, inputting, to a language model which has been trained by machine learning, an examination content that is included in the observation data and that is described in a natural language and causing the language model to output data indicating whether or not the examination content matches the extraction condition; and in the extraction process, the at least one processor determines whether or not the observation data matches the extraction condition, in view of the data outputted by the language model.

(Supplementary Note B5)

The data extraction method according to any one of supplementary notes B1 to B4, in which the extraction condition indicates at least one symptom, and in the extraction process, the at least one processor stores, in the database, the observation data indicating that the patient has the at least one symptom.

(Supplementary Note B6)

The data extraction method according to supplementary note B5, in which the at least one processor causes an output apparatus to output output data that has been generated with use of the observation data stored in the database and that indicates a feature of the at least one symptom, and in a case where new observation data is stored in the database, the at least one processor updates the output data to be outputted by the output apparatus, so that the output data reflects the new observation data.

(Supplementary Note C1)

A data extraction program causing a computer to function as: reception means for receiving designation of an extraction condition on observation data indicating an examination content of a patient; and extraction means for, in a case where the designation is received, starting a process of extracting a piece of observation data which, among observation data that has been stored in at least one target medical institution after reception of the designation, matches the extraction condition designated and storing the piece of observation data in a database.

(Supplementary Note C2)

The data extraction program according to supplementary note C1, in which: the observation data is generated by inputting the examination content to a plurality of data items of an electronic medical record; and the extraction means determines, based on a value of at least one of the plurality of data items which corresponds to the extraction condition in the electronic medical record, whether or not the observation data matches the extraction condition.

(Supplementary Note C3)

The data extraction program according to supplementary note C2, in which the extraction means applies a conversion rule according to the type of the electronic medical record, the conversion rule converting each of the plurality of data items included in the electronic medical record into a standard data item, and determines whether or not the observation data matches the extraction condition, in view of the plurality of data items after conversion.

(Supplementary Note C4)

The data extraction program according to any one of supplementary notes C1 to C3, in which: the data extraction program causes the computer to function as natural language processing means for inputting, to a language model which has been trained by machine learning, an examination content that is included in the observation data and that is described in a natural language and causing the language model to output data indicating whether or not the examination content matches the extraction condition; and the extraction means determines whether or not the observation data matches the extraction condition, in view of the data outputted by the language model.

(Supplementary Note C5)

The data extraction program according to any one of supplementary notes C1 to C4, in which the extraction condition indicates at least one symptom, and the extraction means stores, in the database, the observation data indicating that the patient has the at least one symptom.

(Supplementary Note C6)

The data extraction program according to supplementary note C5, in which the data extraction program causes the computer to function as output control means for causing an output apparatus to output output data that has been generated with use of the observation data stored in the database and that indicates a feature of the at least one symptom, and in a case where new observation data is stored in the database by the extraction means, the output control means updates the output data to be outputted by the output apparatus, so that the output data reflects the new observation data.

(Supplementary Note D1)

An information processing apparatus including at least one processor, the at least one processor being configured to carry out: a reception process of receiving designation of an extraction condition on observation data indicating an examination content of a patient; and an extraction process of, in a case where the designation is received, starting a process of extracting a piece of observation data which, among observation data that has been stored in at least one target medical institution after reception of the designation, matches the extraction condition designated and storing the piece of observation data in a database.

The information processing apparatus may further include a memory. The memory may have stored therein a program for causing the at least one processor to carry out the each of the processes.

(Supplementary Note D2)

The information processing apparatus according to supplementary note D1, in which: the observation data is generated by inputting the examination content to a plurality of data items of an electronic medical record; and in the extraction process, the at least one processor determines, based on a value of at least one of the plurality of data items which corresponds to the extraction condition in the electronic medical record, whether or not the observation data matches the extraction condition.

(Supplementary Note D3)

The information processing apparatus according to supplementary note D2, in which in the extraction process, the at least one processor applies a conversion rule according to the type of the electronic medical record, the conversion rule converting each of the plurality of data items included in the electronic medical record into a standard data item, and determines whether or not the observation data matches the extraction condition, in view of the plurality of data items after conversion.

(Supplementary Note D4)

The information processing apparatus according to any one of supplementary notes D1 to D3, in which: the at least one processor carries out a natural language process of inputting, to a language model which has been trained by machine learning, an examination content that is included in the observation data and that is described in a natural language and causing the language model to output data indicating whether or not the examination content matches the extraction condition; and in the extraction process, the at least one processor determines whether or not the observation data matches the extraction condition, in view of the data outputted by the language model.

(Supplementary Note D5)

The information processing apparatus according to any one of supplementary notes D1 to D4, in which the extraction condition indicates at least one symptom, and in the extraction process, the at least one processor stores, in the database, the observation data indicating that the patient has the at least one symptom.

(Supplementary Note D6)

The information processing apparatus according to supplementary note D5, in which the at least one processor carries out: an output control process of causing an output apparatus to output output data that has been generated with use of the observation data stored in the database and that indicates a feature of the at least one symptom, and an updating process of, in a case where new observation data is stored in the database, updating the output data to be outputted by the output apparatus, so that the output data reflects the new observation data.

(Supplementary Note E)

A non-transitory storage medium storing a data extraction program that causes a computer to carry out: a reception process of receiving designation of an extraction condition on observation data indicating an examination content of a patient; and an extraction process of, in a case where the designation is received, starting a process of extracting a piece of observation data which, among observation data that has been stored in at least one target medical institution after reception of the designation, matches the extraction condition designated and storing the piece of observation data in a database.

REFERENCE SIGNS LIST

1 Information processing apparatus
101 Reception section (reception means)
102 Extraction section (extraction means)
1A Information processing apparatus
101A Reception section (reception means)
102A Extraction section (extraction means)
104A Natural language processing section (natural language processing means)
106A Output control section (output control means)

The invention claimed is:

1. An information processing apparatus comprising at least one processor, the at least one processor being configured to:

receive designation of an extraction condition on observation data indicating an examination content of a patient; and in a case where the designation is received, start a process of extracting a piece of observation data which, among observation data that has been stored in at least one target medical institution after reception of the designation, matches the extraction condition designated and storing the piece of observation data in a database, wherein the observation data is generated by inputting the examination content to a plurality of data items of an electronic medical record; and in the extracting, the at least one processor applies a conversion rule according to the type of the electronic medical record, the conversion rule converting each of the plurality of data items included in the electronic medical record into a standard data item, and determines whether or not the observation data matches the extraction condition, in view of a value of at least one of the plurality of data items after conversion, wherein the at least one processor is further configured to, in response to receiving the designation of the extraction condition, start monitoring storing of observation data in at least one database of the at least one target medical institution, and when new observation data is stored, acquire the new observation data from the at least one database, wherein the monitoring includes repeating access to the at least one database at predetermined time intervals to acquire, at a time, pieces of observation data stored during a predetermined time period, and wherein, in the extracting, the at least one processor stores, in the database, the piece of observation data after structuring the piece of observation data into a predetermined format.

2. The information processing apparatus according to claim 1, wherein:

the at least one processor carries out a natural language process of inputting, to a language model which has been trained by machine learning, an examination content that is included in the observation data and that is described in a natural language and causing the language model to output data indicating whether or not the examination content matches the extraction condition; and in the extracting, the at least one processor determines whether or not the observation data matches the extraction condition, in view of the data outputted by the language model.

3. The information processing apparatus according to claim 1, wherein:

the extraction condition indicates at least one symptom; and in the extracting, the at least one processor stores, in the database, the observation data indicating that the patient has the at least one symptom.

4. The information processing apparatus according to claim 3, wherein the at least one processor carries out:

an output control process of causing an output apparatus to output output data that has been generated with use of the observation data stored in the database and that indicates a feature of the at least one symptom; and an updating process of, in a case where new observation data is stored in the database, updating the output data to be outputted by the output apparatus, so that the output data reflects the new observation data.

5. A data extraction method comprising:

a reception process of, by at least one processor, receiving designation of an extraction condition on observation data indicating an examination content of a patient, the at least one processor, in a case where the reception process is carried out, starting a process of extracting a piece of observation data which, among observation data that has been stored in at least one target medical institution after reception of the designation, matches the extraction condition designated and storing the piece of observation data in a database, wherein the observation data is generated by inputting the examination content to a plurality of data items of an electronic medical record; and in the process of extracting, the at least one processor applies a conversion rule according to the type of the electronic medical record, the conversion rule converting each of the plurality of data items included in the electronic medical record into a standard data item, and determines whether or not the observation data matches the extraction condition, in view of a value of at least one of the plurality of data items after conversion wherein the at least one processor, in response to receiving the designation of the extraction condition, further starts monitoring storing of observation data in at least one database of the at least one target medical institution, and when new observation data is stored, acquires the new observation data from the at least one database, wherein the monitoring includes repeating access to the at least one database at predetermined time intervals to acquire, at a time, pieces of observation data stored during a predetermined time period, and wherein, in the extracting, the at least one processor stores, in the database, the piece of observation data after structuring the piece of observation data into a predetermined format.

6. A computer-readable non-transitory storage medium storing a data extraction program that causes a computer to:

carry out a reception process of receiving designation of an extraction condition on observation data indicating an examination content of a patient; and in a case where the designation is received, start a process of extracting a piece of observation data which, among observation data that has been stored in at least one target medical institution after reception of the designation, matches the extraction condition designated and storing the piece of observation data in a database, wherein the observation data is generated by inputting the examination content to a plurality of data items of an electronic medical record; and in the process of extracting, the computer applies a conversion rule according to the type of the electronic medical record, the conversion rule converting each of the plurality of data items included in the electronic medical record into a standard data item, and determines whether or not the observation data matches the extraction condition, in view of a value of at least one of the plurality of data items after conversion wherein the computer, in response to receiving the designation of the extraction condition, further starts monitoring storing of observation data in at least one database of the at least one target medical institution, and when new observation data is stored, acquires the new observation data from the at least one database, wherein the monitoring includes repeating access to the at least one database at predetermined time intervals to acquire, at a time, pieces of observation data stored during a predetermined time period, and wherein, in the extracting, the computer stores, in the database, the piece of observation data after structuring the piece of observation data into a predetermined format.

* * * * *